US006743171B1

(12) United States Patent
Bowles et al.

(10) Patent No.: US 6,743,171 B1
(45) Date of Patent: Jun. 1, 2004

(54) RELOCATABLE MENTAL FUNCTION TESTING GATEWAY

(76) Inventors: Henry M. Bowles, 1331 St. Charles St., Alameda, CA (US) 94501; Theodore D. Langley, 325 Wawona St., San Francisco, CA (US) 94127-1329

( * ) Notice: Subject to any disclaimer, the term of this patent is extended or adjusted under 35 U.S.C. 154(b) by 0 days.

(21) Appl. No.: 09/566,926

(22) Filed: May 6, 2000

Related U.S. Application Data

(60) Provisional application No. 60/133,174, filed on May 7, 1999, provisional application No. 60/042,577, filed on Apr. 2, 1997, and provisional application No. 60/058,841, filed on Sep. 15, 1997.

(51) Int. Cl.[7] .......... A61B 5/00
(52) U.S. Cl. .......... 600/300
(58) Field of Search .......... 600/300, 558; 273/446, 454; 434/236; 340/5.2

(56) References Cited

U.S. PATENT DOCUMENTS 4,723,625 A * 2/1988 Komlos .......... 600/558
4,755,140 A * 7/1988 Rimland .......... 434/236
5,682,882 A * 11/1997 Lieberman .......... 600/558

* cited by examiner

*Primary Examiner*—Kevin Shaver
*Assistant Examiner*—Brian Szmal
(74) *Attorney, Agent, or Firm*—Crosby, Heafey, Roach & May

(57) ABSTRACT

This invention is a gateway for testing mental function comprising a portable structure that houses one or more mental function testers and an access control device that allows the user to enter a defined area based upon the result of the mental function test. The access control device may either directly control an exit from the gateway or it may dispense a portable indicator of the test results. The gateway may comprise one or more mental function testers that give the same or different tests. The invention also comprises methods of using the gateway, including the steps of assessing a user's mental function and operating the access control device depending upon the assessment. The latter step may comprise permitting the user access to an at-risk activity.

21 Claims, 9 Drawing Sheets

RELOCATABLE MENTAL FUNCTION TESTING GATEWAY

CROSS-REFERENCE TO RELATED APPLICATIONS

This application claims priority from U.S. Provisional Patent Application Serial No. 60/133,174, entitled Relocateable Mental Function Testing Gateway, filed May 7, 1999, and U.S. patent application Ser. No. 09/053,111, filed Apr. 1, 1998, and issued Sep. 5, 2000 as U.S. Pat. No. 6,113,538, which are incorporated herein by reference. Also incorporated herein by reference is U.S. Provisional Patent Application Serial No. 60/042,577, entitled Alertness Testing System, filed Apr. 2, 1997 and U.S. Provisional Patent Application Serial No. 60/058,841, entitled Brain Function Tester for All Ages, filed Sep. 15, 1997. Also incorporated herein by reference are the following disclosure documents filed with the U.S. Pat. No. 394,198, entitled Special Purpose Computer System for Alertness and Readiness Testing, filed Mar. 4, 1996; U.S. Pat. No. 383,562, entitled Multilingual Software and its Use in Dedicated Computer System Used for Alertness and Readiness Testing, filed Mar. 11, 1996; U.S. Pat. No. 399,622, entitled Software and Hardware System to Test Alertness and Fitness, filed Jun. 6, 1996; U.S. Pat. No. 405,957, entitled Nonlinguistic Turnkey Test System for Mental Alertness and Awakeness, filed Oct. 16, 1996; U.S. Pat. No. 422,723, entitled Alertness Testing System with Alertness Gauge, filed Aug. 6, 1997; U.S. Pat. No. 423,524, entitled Medical, Visual and Psychomotor Testing System, filed Aug. 21, 1997; and U.S. Pat. No. 433,824 Tester for Early Detection of Alzheimer's Disease, filed Mar. 23, 1998.

BACKGROUND OF THE INVENTION

1. Field of the Invention

The present invention relates devices and methods for testing the mental function of a user and utilizing the results of the test to control access to a specified activity.

2. Description of the Background Art

Accidents in the workplace cost many millions of dollars, hundreds of lives, and damage to the environment every year. The majority of these accidents are caused by human error. Human error has, of course, many causes, but it is most prevalent when an operator is impaired from lack of sleep, illness, or is under the influence of drugs or alcohol. In the U.S., 7.5 million workers in high-risk occupations are required to take random blood or urine tests to deter the use of drugs and alcohol on the job, a requirement that has helped reduce accidents. However, fatigue, illness and stress are more common causes of impairment than are the effects of drugs or alcohol. Accidents continue to occur in large part because workers are impaired by exhaustion, stress, and side effects from prescription medications or from a combination of these factors. There is therefore an urgent need for a way to screen workers for all impairment factors and causes before they begin work. Screening of this kind should be sensitive to impairment regardless of its cause, should be simple and quick, and should insure the maintenance of worker privacy.

SUMMARY OF THE INVENTION

This invention meets these and other needs and comprises a gateway for testing mental function. Generally, the gateway comprises a portable structure that houses one or more mental function testers. The gateway also comprises an access control device that allows the user to enter a defined area based upon the result of the mental function test. The access control device may either directly permit exit from the gateway or it may dispense a portable indicator of the test results. The portable indicator may comprise a token, stamp, receipt, or the like or may comprise information recorded to a portable memory device. The gateway may comprise one or more mental function testers that give the same or different tests. Accordingly, the gateway may be used to test multiple users simultaneously and may give the same or different tests. The gateway may house the tester either inside the structure or outside. Further, the gateway may comprise wheels. The invention also comprises methods of using the gateway, including the steps of assessing a user's mental function and operating the access control device depending upon the assessment. The latter step may comprise permitting the user access to an at-risk activity.

The gateway is a portable, special-purpose enclosure whose main purpose is to function as a gateway into an area where one or more at-risk activities will occur, or will begin or are already taking place. It controls access to, or entry into, the area. If the person is denied entry into time area, they cannot engage in, or begin, the at-risk activity, such as driving a truck or taxi or doing welding.

The at-risk activity can be employment or leisure or entertainment, by adults or by children, or it can be in the Military or in law enforcement agencies. The at-risk activity can involve various degrees of physical activity and coordination, such as driving a truck or school bus, or welding, or engaging in a sport such as football, skiing, roller skating, or engaging in a skilled profession such as dentistry or surgery.

On the other hand, the at-risk activity can involve little physical activity but a lot of mental activity and decision-making such as being a radar operator, or an air traffic control operator, or operating a cargo ship or a ferry, or flying an airplane, or monitoring the control panel of a nuclear power plant.

These gateways contain one or more electronic devices that test people for mental alertness, mental fitness and normal mental functioning. A person enters one end of the enclosure and takes a mental function test. If they pass the test, they go out the other end through a gate, turnstile or door into the area where the at-risk activity is being or will be conducted. If they do not pass the test, they cannot get into the area and are thereby denied access to the at-risk activity.

BRIEF DESCRIPTION OF THE DRAWINGS

The aforementioned advantages of the invention, as well as additional advantages thereof, will be more fully understood from a detailed description of a preferred embodiment when taken in conjunction with the accompanying drawings in which.

DETAILED DESCRIPTION OF THE INVENTION

This invention is a gateway that controls access into an area where one or more at-risk activities will occur, or will begin or are already taking place. The gateway is a portable structure that comprises a mental function tester to assess the mental fitness of the user and an access control to selectively permit or deny entry to the at-risk activity area. If the user fails to meet the criteria established by the mental function tester, the user is denied entry into the area and cannot engage in, or begin, the at-risk activity, such as driving a truck or taxi or welding.

The at-risk activity can be employment or leisure or entertainment, by adults or by children, or it can be in the Military or in law enforcement agencies. The at-risk activity can involve various degrees of physical activity and coordination, such as driving a truck or school bus, or welding, or engaging in a sport such as football, skiing, roller skating, or engaging in a skilled profession such as dentistry or surgery.

On the other hand, the at-risk activity can involve little physical activity but a lot of mental activity and decision-making such as being a radar operator, or an air traffic control operator, or operating a cargo ship or a ferry, or flying an airplane, or monitoring the control panel of a nuclear power plant.

The mental function tester of the gateways comprises one or more electronic devices that test people for mental alertness, mental fitness and normal mental functioning. A user enters one end of the enclosure and takes one or more mental function tests. If the user passes the test, the user is given access, through a gate, turnstile, door, or other suitable means, into the area where the at-risk activity is being or will be conducted. If the user does not pass the test, the user is denied access to the at-risk activity area.

Preferably, the gateways of the invention are self-contained, single-purpose, dedicated units with the sole purpose of testing users for alertness and mental fitness before they engage in a potentially dangerous or hazardous activity. The testing function is carried out by one or more alertness and mental fitness testers housed by the gateways, either inside the unit or on the outside of it, as described below and shown in FIGS. 1–7.

Typically, the gateway provides a self-contained environment for testing multiple users with multiple testers. In these embodiments, the gateway has an interior outfitted with doors, partitions, and windows where required. A mental function or alertness tester is stationed in each partitioned section, either on a small table, or on a shelf, or wall-mounted. Positioning the testers inside the gateway ensures a constant protected environment for users each time they take the test, regardless of the outside weather and regardless of it being daytime or nighttime. This constant environment presents an ideal condition in which to take the same test(s) many times.

Figure 1:
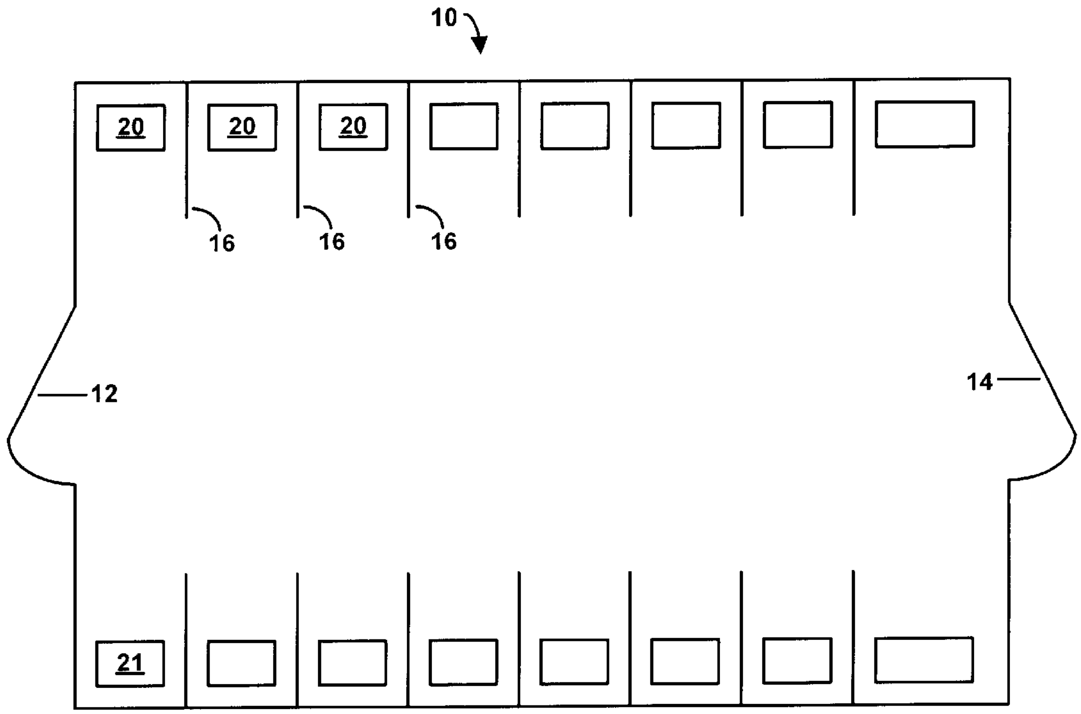
FIG. 1 is a schematic view of a gateway mental function tester of the invention having multiple stations with the entry and exit at opposite ends.

For example, FIG. 1 schematically shows the floor plan of gateway 10, which has an entry 12 and an exit 14 positioned at opposite ends of the gateway. Partitions 16 form alcoves 18 to house testers 20. A user enters gateway 10 through entry 12 and is permitted to leave through exit 14 only if the user is validated by tester 20. A different tester 21 may be provided so that different users may be screened by different criteria, or to allow different screening of the same user. Multiple testers permit the simultaneous testing of a number of users. The size and configuration of the gateway can be optimized for various uses, for example gateway 10 can be approximately 12 ft by 24 ft.

Figure 2:
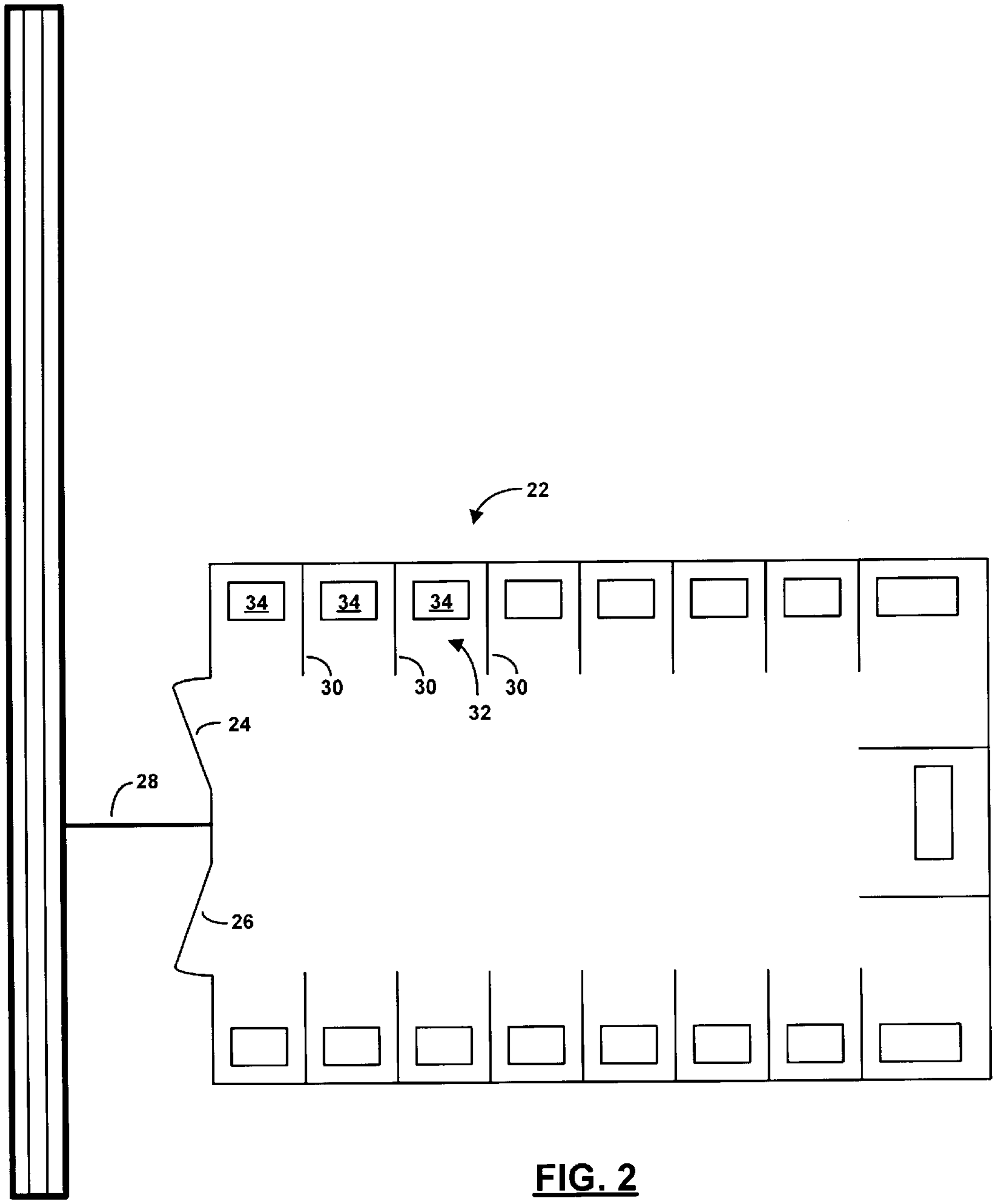
FIG. 2 is a schematic view of a gateway mental function tester of the invention having multiple stations with the entry and exit at the same end.

In an alternative embodiment, shown in FIG. 2, gateway 22 has an entry 24 and an exit 26 positioned at the same end. A barrier 28 prevents users from bypassing gateway 22. As above, gateway 22 may be provided with partitions 30 to form alcoves 32 for testers 34.

Figure 3:
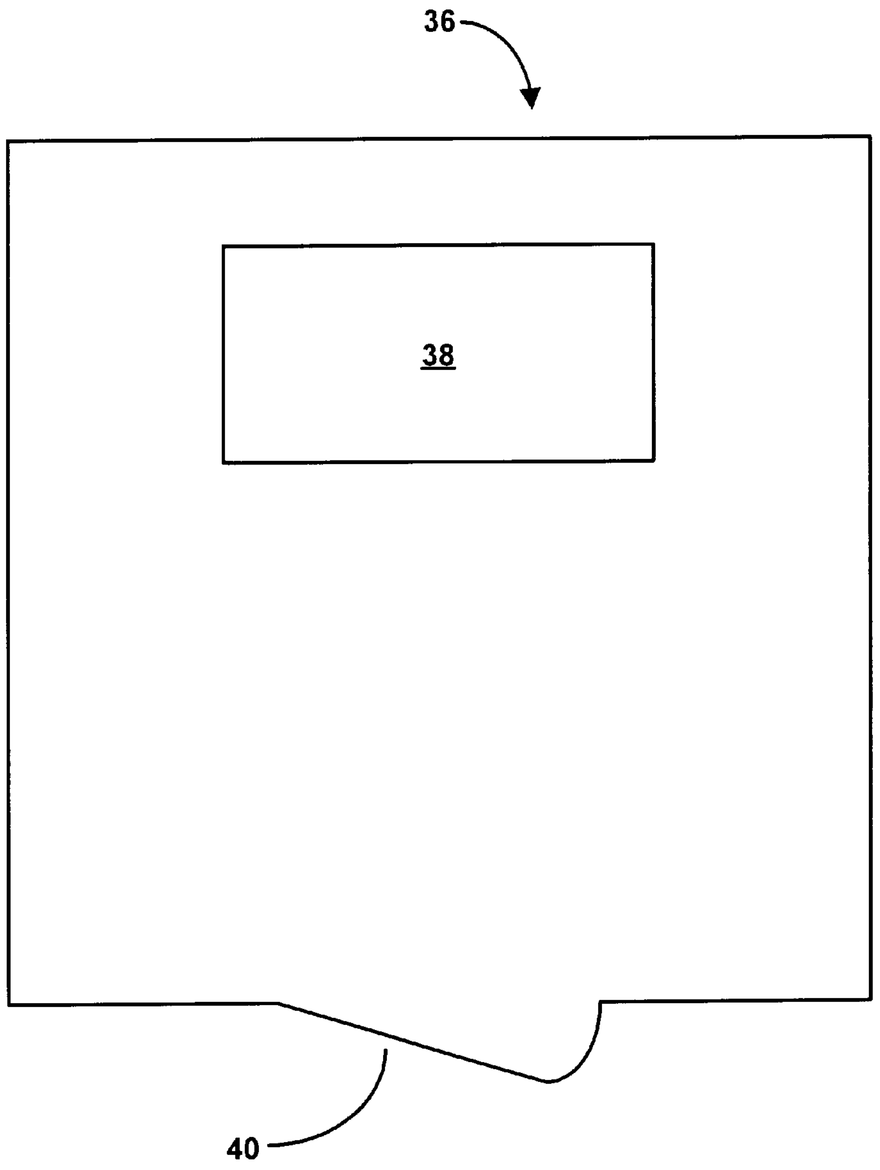
FIG. 3 is a schematic view of a gateway mental function tester of the invention having a single station.

The gateways of the invention may easily be adapted for single tester use. As shown in FIG. 3, gateway 36 comprises a relatively small structure, configured to house a single tester 38. Privacy and a controlled environment are provided by door 40. Since gateway 36 is sized for one person at a time, it is preferably of the approximate size of a telephone booth or somewhat larger, for example, a voting booth.

Figure 4A:
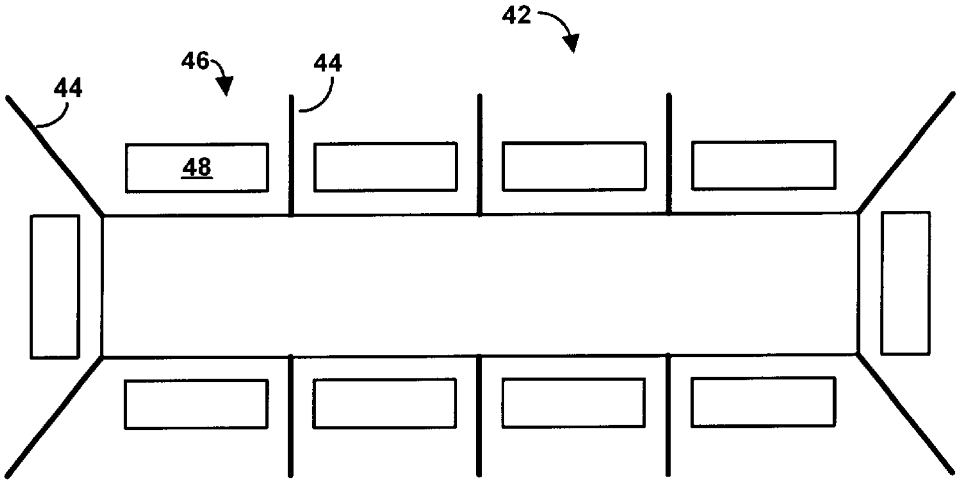
FIGS. 4*a* and 4*b* are schematic views of a stand type gateway mental function tester of the invention.
Figure 4B:
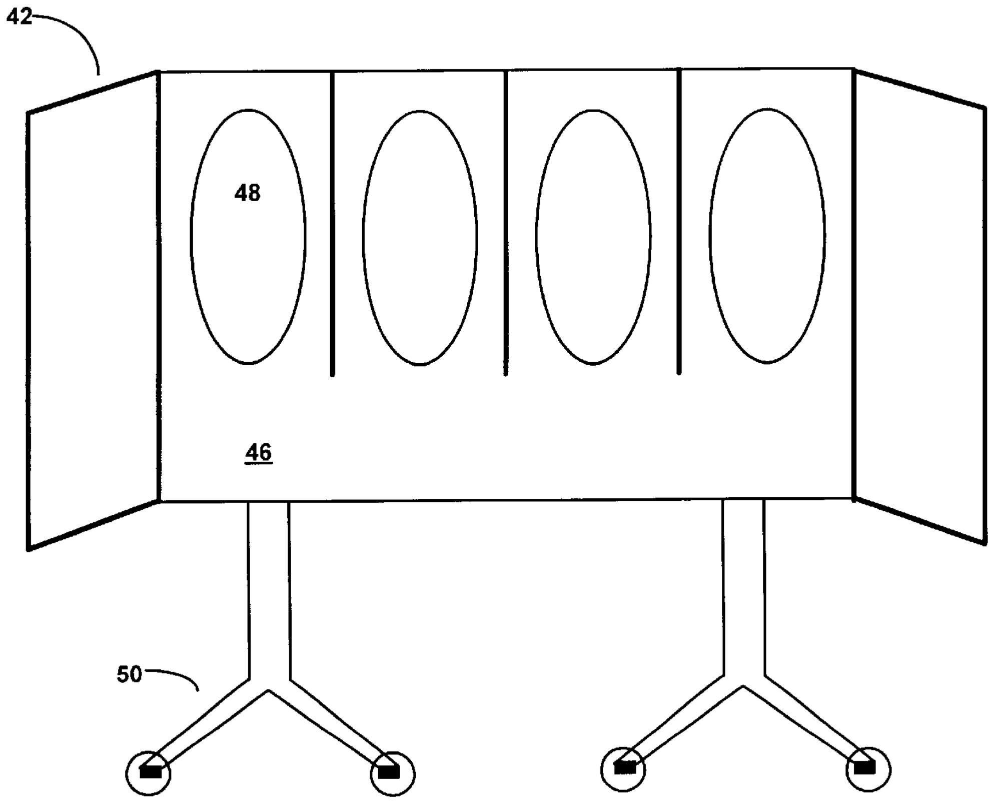

Although all the gateways of the invention are designed to be portable, certain embodiments are particularly mobile. For example, FIG. 4*a* shows a top view and FIG. 4*b* shows a side view of gateway 42 having a stand configuration similar to a chalkboard.

Figure 5A:
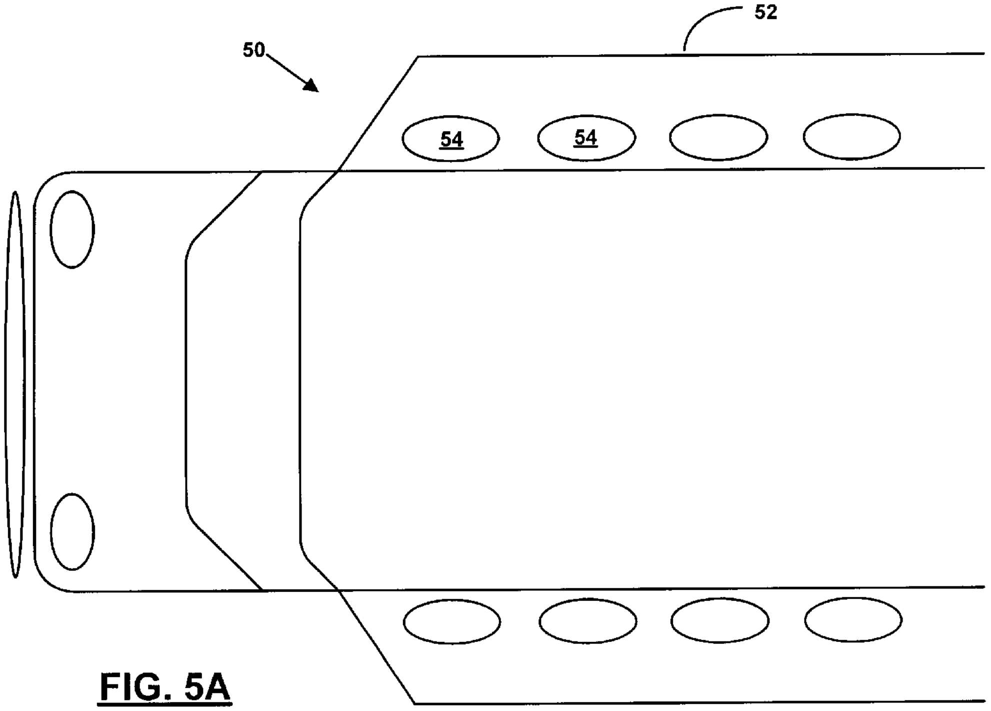
FIGS. 5*a* and 5*b* are schematic views of a vehicle-mounted gateway mental function tester of the invention.
Figure 5B:
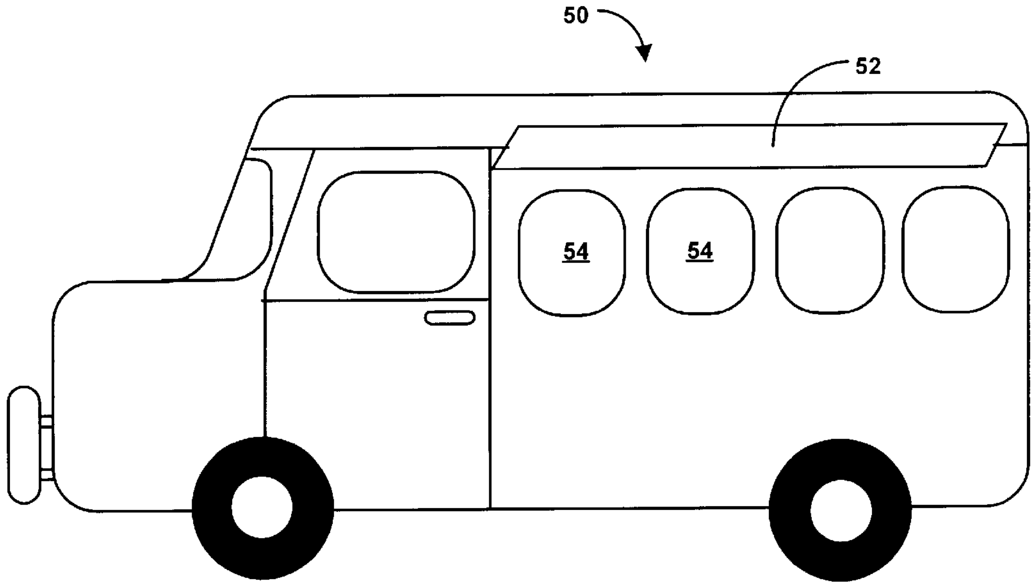

Generally, gateway 42 has partitions 44 to form alcoves 46 that house testers 48. Wheel assembly 50 provides maximum portability, and can be fixed, retractable, or motorized. Alternatively, the wheels can be omitted. In this embodiment, testers 48 are preferably wall-mounted or located on shelves. Gateway 42 may be about 1 ft by 6 ft, or any other suitable dimension. FIG. 5*a* shows a top view and FIG. 5*b* shows a side view of vehicle-based gateway 50. Hinged canopy 52 swings up to provide access to testers 54 when the gateway is in use. During transit and for storage, canopy 52 can be dropped to protect testers 54. Alternatively, testers can be located inside gateway 50. Gateway 50 can be motorized or configured to be pulled.

FIG. 6 shows a variety of possible barrier arrangements for use with the gateways of this invention. FIGS. 6*a*–*c* show a schematic view of embodiments having an entry 56 and exit 58 at opposite sides of the gateway 60. In FIG. 6*a*, gateway 60 is positioned adjacent an existing barrier 62, typically either a wall or fence, having an opening 64, typically a gate, door or turnstile. Users leaving from exit 58 are directed to opening 64 by boundaries 65, which may comprise stanchions or any other suitable device. In FIG. 6*b*, gateway 60 is butted against barrier 62, so that exit 58 opens directly into opening 64.

Figure 6A:
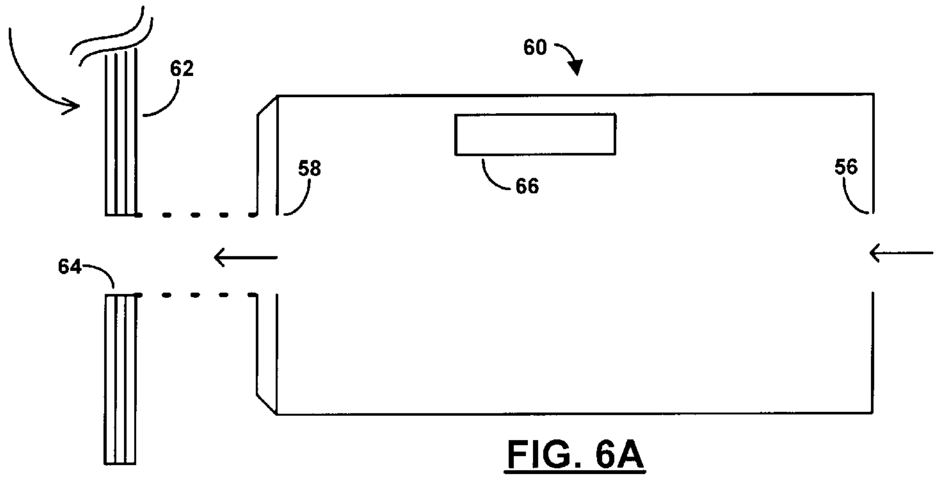
FIGS. 6*a*, 6*b*, 6*c* and 6*d* are schematic views of gateway mental function testers of the invention having varying barrier configurations.
Figure 6B:
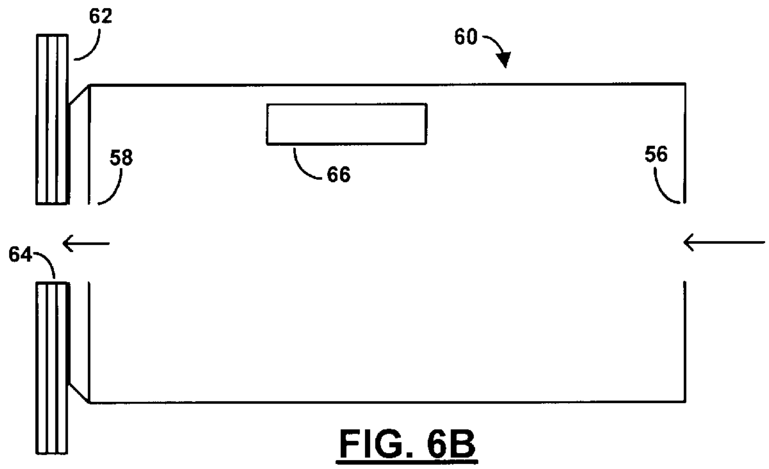
Figure 6C:
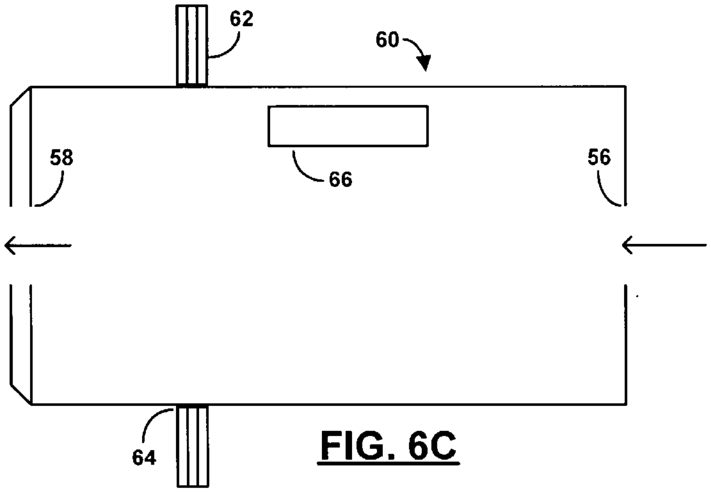
Figure 6D:
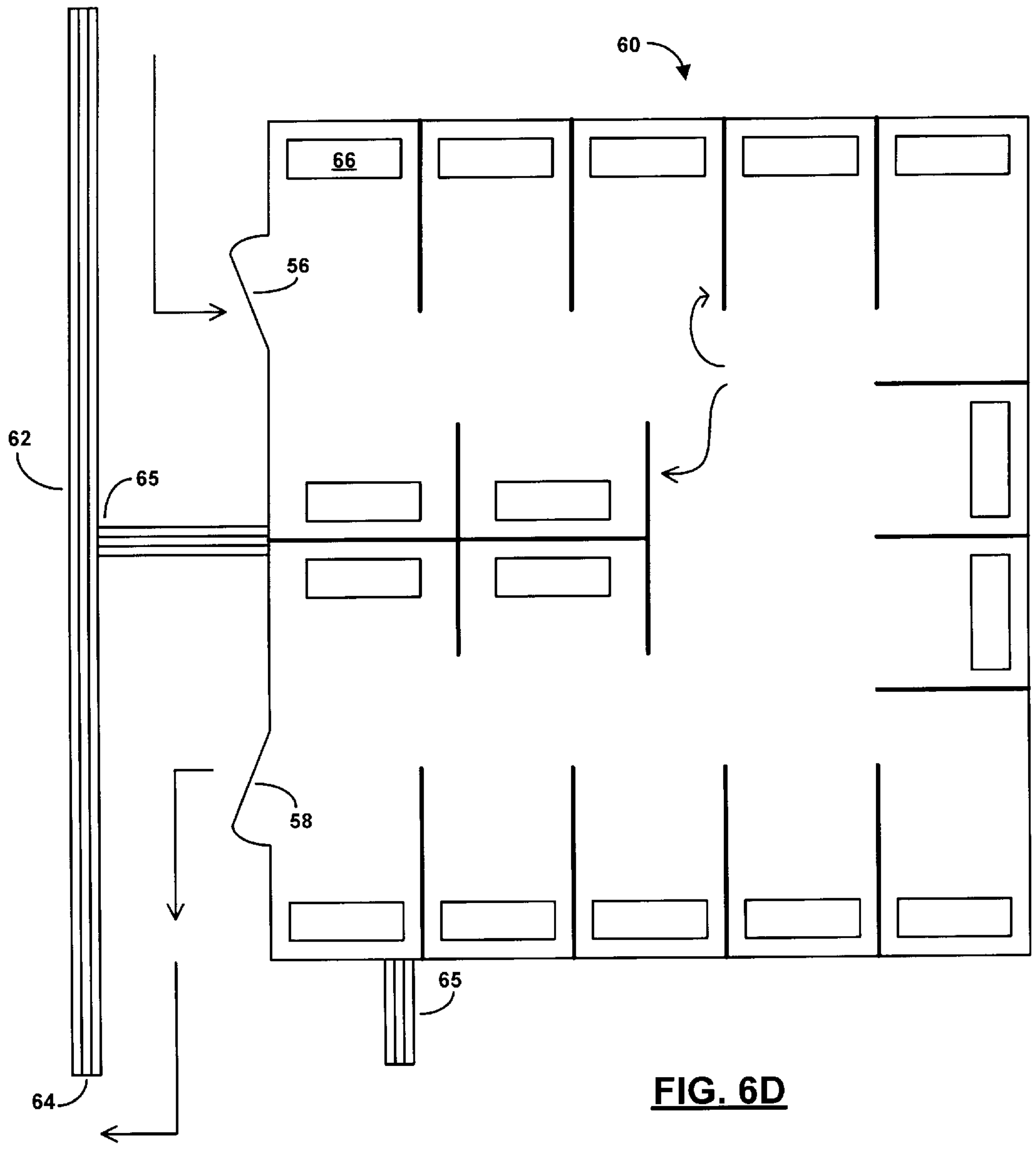

FIG. 6*c* shows gateway 60 is positioned through opening 64. Finally, FIG. 6*d* shows gateway 60 with entry 56 and exit 58 on the same end. Boundaries 65 prevent users from bypassing gateway 60. In each of these embodiments, users enter gateway 60 through entry 56, have their mental function screened by testers 66, and, if validated, are allowed to exit through exit 58 where they can enter the at-risk area through opening 64.

The gateways of the invention can contain different types of mental function testers, and different people can be assigned to take different tests, but they are primarily mental function tests, even though the tester may include testing a non-mental function such as blood sugar or exhaled carbon dioxide, etc.

The pass-through type of gateways described herein, such as those shown in FIGS. 1, 2, 6, and 7, can also function as security controls, since a person's employment ID card can be inserted into a reader to open a gate, or shown to a Security Guard to enter the work area. This ID card can also contain the results of the mental function test, in a portable memory device such as a smartcard, memory button, or other portable memory device. This same security function can occur if the results of the mental function test(s) are printed on a paper or plastic receipt or ticket, or stamped on the back of the hand with either visible ink, or with invisible ink in order to be read under ultraviolet light. Alternatively, the gateway comprises a dispenser that dispenses a token if a tester determines the person's mental function is normal.

The gateways need electrical power to operate the testers and for other functions such as lights and HVAC, depending on the size and if the testers are inside or outside of the gateway. When the testers are located inside the gateway, it is preferable for the environment to be as controlled as possible from day to day, so preferably HVAC would be used to control temperature, humidity, lighting and sound. Depending upon the electrical requirements, the gateway may comprise battery storage, generators, solar collectors, wind-power collectors, or connections for accessing an outside supply of electricity. In environments where there may be explosive gasses such as in a refinery, or in a petroleum, or on an oil drilling platform, or near a coal mine, the gateways of the invention can be wired and outfitted to meet the requirements of being explosion-proof.

The gateways of the invention may be outfitted with or without wheels. For example, the gateway can resemble a trailer, regardless of size, when it has wheels attached. For semi-permanent use, the wheels may be removed, but they can be reattached. Alternatively, a gateway can be a container without wheels. This type of embodiment would be normally carried by a vehicle, or by a crane, or wagon, or helicopter, ship or other suitable means. The container type of embodiment need not be built with wheels or intended to have wheels, rather it is configured to be carried or dragged.

For some embodiments of the invention, it is impossible or undesirable to have the tester directly control the exit. Accordingly, a different type of access control device may be required. For example, a signal such as a green light could indicate to a security person that the user passed the test and the security person could let them into the area. Alternatively, the user would employ a portable indicator that would be proof that the user passed the test. This portable indicator could be an electronic PASS code in a memory device such as a smartcard, memory button, or other portable memory device, or it could be a non-electronic indicator such as a token, a paper or plastic receipt or ticket, or it could be an inked stamp on the user's ticket or ID badge, or it could be an inked mark stamped on the back of the user's hand. The user would then use this indicator to gain entrance into the at-risk area by going through a door, gate or turnstile, or past a Security Guard, etc. If a user tried to get through the door, etc. without the portable indicator, an alarm would be triggered, either auditory, visual, silent, for example. Optionally, the portable indicator would expire after a certain duration, such as 3 minutes, to enhance security.

Additional examples of gateway configurations include:

1. a trailer with wheels that is moved to a certain place and then used there either temporarily or permanently, either on its wheels or jacked up off its wheels, with testers inside the unit;
2. a large box, similar in size to an office trailer, which is transported on a truck or crane, and then deposited in a certain location, either temporarily or permanently, with testers inside the unit;
3. a container such as the trailer of a tractor-trailer, which drives from location to location, and stays for a short time each day, such as when a new shift of workers comes in, or stays a longer time, such as weeks or months while work is being done at a certain location, and then it moves on to a new location, with testers inside the unit;
4. a truck, similar to a large "lunch truck" or "sandwich and beverage truck" that drives from location to location, such as at the start of each shift, and stays only long enough to test the workers coming to work at that location for that shift, with testers outside the unit, as shown in FIG. 5.
5. a moveable stand, similar to a chalkboard on wheels, which has testers on one side only, or on both sides, and is wheeled around by hand from location to location, or kept in one location for a long time, which would be used primarily indoors as a chalkboard would be, but could be taken outdoors in good weather, with testers outside the unit, as shown in FIG. 4.
6. an enclosure, which contains only one Tester, can be used as those shown in FIGS. 6 and 7, but it would have only one Tester, instead of several.

In employment, including the military or recreation, this invention is used as an access control, to allow people to enter certain at-risk areas or to use certain at-risk devices. In medical applications, this invention provides a convenient method of testing many people quickly, such as screening for Alzheimer's Disease. In law enforcement, this invention can be used to randomly (or non-randomly) test drivers for sobriety at mental alertness checkpoints, and it can be used to test law enforcement personnel for mental alertness, particularly for dangerous fatigue after long hours on the job. In the maritime industry, including offshore oil well drilling, it can be used to test workers for mental fitness (a.k.a. Fitness for Duty) by testing for some potential debilitating factors, which usually do not apply to land-based employment, such as seasickness. As such, the gateways of the invention can be used to check for fitness for duty, fitness for work, alertness, sobriety and safety as well as for medical screening or security control.

The gateways of the invention will increase safety by decreasing accidents where the users are engaging in at-risk activities, such as driving school buses, monitoring control panels, and even skiing and riding bicycles. It will decrease accidents by screening out those users who are not normally alert and normally mentally fit, regardless of time cause. It follows logically that if impaired persons are not allowed to participate in at-risk activities, then the statistical probability of accidents, both major and minor, will be reduced. The gateways will also screen out people who are mentally impaired by factors such as substance use, fatigue, seasickness, or anything that can impair normal mental functioning. Examples of medical uses include early detection of mental function diseases such as Alzheimer's Disease, brain tumors, etc A multiple station gateway on wheels would be very useful to test many people for mental functioning as a screening method to detect mental problems early so they can be treated. Alzheimer's Disease and brain tumors are examples of neurological diseases, which can be treated effectively if detected early. In these embodiments, the could go to various neighborhoods of low income inner city areas to give free or low-cost testing to large numbers of persons to screen them for early signs of neurological diseases such as Alzheimer's and tumors. The gateways could also go to rural areas and small towns to screen large numbers of people who would not otherwise have convenient access to such neurological tests. Another example of a medical use, it to position gateways at hospitals and medical centers, so people could be tested quickly and conveniently for mental functions before they go in for routine physical exams. Such gateways preferably utilize portable memory devices to store baselines and data allowing ready comparison of many years of data to facilitate early diagnosis of slow onset neurological diseases, such as Alzheimer's Disease and many types of brain tumors.

Yet another application for the gateways of the invention includes use at places of employment where the employer provides time mental function testing on an optional basis, to give feedback to workers on how they are functioning when they report for work. After the test, regardless of what kind of mental function test is given, the user would see some kind of display on the screen or be given a printed readout of their state of alertness and/or mental functioning. The worker would then decide if they will work that day, or if they will ask for less hazardous work for that day, or even if they should just take a nap.

Another example of gateway use is at Interstate Rest Stops, gas stations, restaurants and taverns, where people could take the test(s) and decide if they are mentally fit enough to continue driving, or if they should take a nap. In addition, at gas stations, there could be the added incentive that, if a person scored within their normal daily range of variation, they could use their smartcard to get a discount with their gasoline purchase. In this case, their smartcard could be their employment ID smartcard, or it could be a separate smartcard issued by the petroleum company.

Gateways of the invention can also be used as sobriety and safety checkpoints. The testers inside such gateways are those which test general alertness and general normal brain functions, either by computer tests, or by recording electrodes put on the head, or by measuring some physiological index such as a retinal scan, or iris scan, or some other method which measures normal brain functioning.

In embodiments with gateways that accept portable memory devices from each user, then each user to be tested mould have their own memory device with their own predetermined normal baseline on it and when they take the test, they would be compared to their own normal brain function baseline. This memory device which contains a person's own normal baseline could be the same as that which is used at their place of employment for daily "Fitness for Work" testing or it could be built into their driver's license. If it is built into their driver's license, it may be employed by all users or required only for those persons convicted of DWI or DUI.

The gateways of the invention can also be adapted to use in the military, where they would be located at the entrances to military bases, or at the entrances to motor-pools, or at the entry gangplanks to ships. This use can also be on board ships, such as aircraft carriers, where pilots would have to take a mental function test before getting into their airplane. Similarly, gateways can be adapted to screen for work fitness in many different types of employment, such as house painters, roofers, truck drivers, taxi and limousine drivers, ambulance drivers, for surgeons before surgery, for air traffic controllers, for maritime workers, refinery workers, for assembly line workers, coal mines, etc. For some types of work, such as construction workers and highway crews, it is preferably to power the gateways by portable generators and configure the gateways for maximum portability, such as on wheels and moved from site to site, or carried on flat-bed trucks, or transported by helicopter from site to site.

What is claimed is:

1. A gateway for testing mental function comprising:

a portable structure;

a mental function tester housed by the structure;

an entry and an exit; and an access control device;

wherein the access control device opens the exit when the mental function tester validates a user.

2. The gateway of claim 1, wherein the access control device comprises a signal.

3. The gateway of claim 1, wherein the access control device comprises a portable indicator dispenser.

4. The gateway of claim 3, wherein the portable indicator dispenser records a result from the mental function tester to a portable memory device.

5. The gateway of claim 3, wherein the portable indicator dispenser dispenses a token.

6. The gateway of claim 3, wherein the portable indicator dispenser dispenses a stamp.

7. The gateway of claim 3, wherein the portable indicator dispenser dispenses a receipt.

8. The gateway of claim 1, further comprising a plurality of mental function testers.

9. The gateway of claim 8, wherein the gateway is configured to simultaneously test multiple users.

10. The gateway of claim 8, wherein the plurality of mental function testers screen for different criteria.

11. The gateway of claim 1, wherein the mental function tester is housed inside the structure.

12. The gateway of claim 1, wherein the portable structure comprises wheels.

13. The gateway of claim 12, wherein the wheels are removable.

14. A gateway for testing mental function comprising:

a portable structure;

a mental function tester housed by the structure; and an access control device;

wherein the mental function tester is housed outside the structure.

15. The gateway of claim 14, wherein the portable structure comprises wheels.

16. The gateway of claim 14, wherein the structure comprises a stand configuration.

17. The gateway of claim 15, wherein the structure comprises a vehicle.

18. A method for testing mental function of a user comprising the steps of:

a) providing a portable structure, a mental function tester housed by the structure and an access control device;

b) assessing the mental function of the user with the mental function tester;

c) operating the access control device depending upon the assessment of the mental function of the user; and d) opening an exit via operation of the access control device when the mental function tester validates the user.

19. The method of claim 18, wherein the step of operating the access control device comprises allowing the user to participate in an at-risk activity if the user is validated by the mental function tester.

20. The method of claim 18, wherein the step of operating the access control device comprises recording the results of the assessment on a portable memory device.

21. The method of claim 18, wherein the step of operating the access control device comprises indicating the results of the assessment.

* * * * *